United States Patent [19]

Stanley et al.

[11] Patent Number: 4,863,737
[45] Date of Patent: Sep. 5, 1989

[54] COMPOSITIONS AND METHODS OF MANUFACTURE OF COMPRESSED POWDER MEDICAMENTS

[75] Inventors: Theodore H. Stanley, Salt Lake City; Brian Hague, West Valley, both of Utah

[73] Assignee: University of Utah, Salt Lake City, Utah

[21] Appl. No.: 60,045

[22] Filed: Jun. 8, 1987

Related U.S. Application Data

[63] Continuation-in-part of Ser. No. 729,301, May 1, 1995, Pat. No. 4,671,953.

[51] Int. Cl.$^4$ .............................................. A61K 9/68
[52] U.S. Cl. ..................................... 424/440; 424/439
[58] Field of Search ............... 426/104, 134, 658, 660, 426/801; 424/435, 439, 440, 499; 514/270

[56] References Cited

U.S. PATENT DOCUMENTS

| | | |
|---|---|---|
| D. 93,287 | 9/1934 | Reed . |
| 109,677 | 11/1870 | Seitz . |
| D. 117,455 | 11/1939 | Parr . |
| D. 117,456 | 11/1939 | Parr . |
| 1,430,642 | 10/1922 | Gross . |
| 1,593,858 | 7/1926 | Venable . |
| 1,847,415 | 3/1932 | Snell . |
| 1,915,614 | 6/1933 | Parker . |
| 1,971,560 | 8/1934 | Guyon ................................ 90/16 |
| 2,096,611 | 10/1937 | Ellestad ............................. 99/183 |
| 2,208,120 | 7/1940 | Coleman ........................... 107/82 |
| 2,246,778 | 6/1941 | Cahoon ............................. 99/138 |
| 2,295,042 | 9/1942 | Llewellyn .......................... 43/34 |
| 2,323,656 | 7/1943 | Helfenstein ...................... 43/36 |
| 2,388,533 | 11/1945 | Edmondson et al. ............ 128/202 |
| 2,469,589 | 5/1949 | Barricini .......................... 99/138 |
| 2,488,272 | 11/1949 | Davis ............................... 57/154 |
| 2,499,734 | 3/1950 | Edmondson et al. ............ 128/197 |
| 2,508,560 | 5/1950 | Adams .............................. 43/36 |
| 2,553,446 | 5/1951 | Edmondson et al. ............ 128/188 |
| 2,857,908 | 10/1958 | Cornfield .......................... 128/15 |
| 2,897,624 | 8/1959 | Yakel et al. ....................... 43/36 |
| 2,915,061 | 12/1959 | Edmondson et al. ............ 128/188 |
| 2,926,121 | 2/1960 | Hobbs et al. .................... 424/440 |
| 2,963,404 | 12/1960 | Hammer et al. ................. 167/82 |
| 3,169,907 | 2/1965 | Heusser et al. .............. 424/440 X |
| 3,172,179 | 3/1965 | Schafer ............................. 24/91 |
| 3,192,924 | 7/1965 | Edmondson et al. ............ 128/188 |
| 3,210,247 | 10/1965 | Suranyi ............................ 514/270 |
| 3,264,115 | 8/1966 | Davis ............................... 99/138 |
| 3,271,256 | 9/1966 | Frey ................................. 167/82 |

(List continued on next page.)

FOREIGN PATENT DOCUMENTS

| | | |
|---|---|---|
| 0001907 | 5/1979 | European Pat. Off. . |
| 2441341 | 6/1980 | France . |
| 132404 | 9/1978 | German Democratic Rep. . |
| 100714 | 8/1981 | Japan . |
| 118511 | 7/1982 | Japan . |
| 1083896 | 9/1967 | United Kingdom . |

(List continued on next page.)

OTHER PUBLICATIONS

Dyer, "Medicated Candies" Q.S. 4 (1953).

(List continued on next page.)

*Primary Examiner*—Thurman K. Page
*Attorney, Agent, or Firm*—Workman, Nydegger & Jensen

[57] ABSTRACT

Compositions and methods of manufacture for producing a medicament composition capable of absorption through the mucosal tissues of the mouth, pharynx, and esophagus. The present invention relates to such compositions and methods which are useful in administering drugs in a dose-to-effect manner such that sufficient drug is administered to produce precisely a desired effect. The invention also relates to a manufacturing technique that enables a therapeutic agent or drug to be incorporated into a flavored confectionary base and to compress or otherwise attach the solid confectionary mixture onto an appliance or holder. Employing the present invention, the drug may be introduced into the patient's bloodstream almost as fast as through injection, and much faster than using the oral administration route, while avoiding the negative aspects of both of these methods. The present invention achieves these advantages by incorporating the drug into a compressed powder "candy" matrix. The pH and pKa of the powder matrix can be modified to increase the absorption of the drug through the mucosal tissues.

52 Claims, 1 Drawing Sheet

U.S. PATENT DOCUMENTS

| | | | |
|---|---|---|---|
| 3,341,414 | 9/1967 | Cherkas et al. | 167/82 |
| 3,344,030 | 9/1967 | Stevens et al. | 514/270 X |
| 3,399,673 | 9/1968 | Jones et al. | 128/188 |
| 3,418,743 | 12/1968 | Halvorsen | 43/35 |
| 3,429,308 | 2/1969 | Russell | 424/440 X |
| 3,493,652 | 2/1970 | Hartman | 424/435 X |
| 3,556,811 | 1/1971 | Smith | 99/134 |
| 3,797,494 | 3/1974 | Zaffaroni | 128/268 |
| 3,816,953 | 6/1974 | Hameen-Anttila | 43/35 |
| 3,867,927 | 2/1975 | Hergott | 128/15 |
| 3,943,928 | 3/1976 | Lariccia et al. | 128/260 |
| 3,996,934 | 12/1976 | Zaffaroni | 128/268 |
| 4,060,084 | 11/1977 | Chandrasekaran et al. | 128/260 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,139,627 | 2/1979 | Lane et al. | 424/267 |
| 4,168,308 | 9/1979 | Wretlind et al. | 514/270 X |
| 4,169,885 | 10/1979 | Raaf et al. | 424/440 |
| 4,226,848 | 10/1980 | Nagai et al. | 424/440 X |
| 4,292,299 | 9/1981 | Suzuki et al. | 424/440 X |
| 4,307,075 | 12/1981 | Martin | 424/28 |
| 4,346,709 | 8/1982 | Schmitt | 128/260 |
| 4,372,942 | 2/1983 | Cimiluca | 424/16 |
| 4,390,520 | 6/1983 | Nagai et al. | 424/28 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,485,087 | 11/1984 | Otsuka et al. | 424/28 |
| 4,517,173 | 5/1985 | Kizawa et al. | 424/435 |
| 4,529,589 | 7/1985 | Davydov et al. | 424/440 X |
| 4,551,329 | 11/1985 | Harris et al. | 424/22 |
| 4,572,832 | 2/1986 | Kigasawa et al. | 424/440 X |
| 4,588,580 | 5/1986 | Gale et al. | 424/21 |
| 4,671,953 | 6/1987 | Stanley et al. | 424/440 |

FOREIGN PATENT DOCUMENTS 1171691 11/1969 United Kingdom .
418841 5/1983 United Kingdom .

OTHER PUBLICATIONS

Brown, "Absorption of Analgesics from the Buccal Mucous Membrane", 196 The Practitioner, 125 (1966).

Beckett et al., "Buccal Absorption of Basic Drugs and its Application as an In Vivo Model of Passive Drug Transfer through Lipid Membrands," 19 J. Pharm. Pharmac. 31S (1967).

Dearden et al., "Buccal Absorption as a Parameter of Analgesic Activity of Some P-Substituted Acetanilides," 23 Journal Pharm. Pharmac. 73S (1971).

Dearden et al., "A New Buccal Absorption Model," 23 J. Pharm. Pharmac. 68S (1971).

Dollery et al., "Differences in the Metabolism of Drugs Depending Upon Their Routes of Administration," 179 Annals of te New York Academy of Sciences 108 (1971).

Dobkin, "Buprenorphine Hydrochloride: Determination of Anaglesic Potency," 24 Canadian Anaesthesiology Society Journal 186 (1977).

Edge et al., "Analgesic Effects of Sublingual Buprenorphine," 34 Anaesthesia 463 (1979).

Fry, "Relief of Pain After Surgery," 34 Anaesthesia 549 (1979).

Bullingham et al., "Sublingual Buprenorphine Used Postoperatively: Clinical Observations and Preliminary Pharmacokinetic Analysis," 12 Br. J. Clin. Pharmac. 117 (1981).

Hug et al., "The Pharmacokinetics of Fentanyl," Janssen Pharmaceutica Inc. (1981).

Ellis et al., "Pain Relief After Abdominal Surgery-A Comparison of I.M. Morphine, Sublingual Buprenorphine and Self-Administered I.V. Pethidine," 54 Br. J. Anaesth. 421 (1982).

Port et al., "Carfentanil: The Primate Experience," American College of Veterinary Anesthesiologist (1983).

Port et al, "Topical Narcotic Anesthesia," 59 Anesthesiology (1983).

Windholz et al., "The Merck Index," published by Merck & Co., Inc., pp. 575, 795, 796, and Appendix 3 (1983).

Abrams, "New Nitrate Delivery Systems: Buccal Nitroglycerin", vol. 105 American Heart Journal, pp. 848-854 (May 1983).

White et al., "Comparative Pharmacology of Intravenous Anesthetics-A Model for Determining Dosage Requirements and Therapeutic Concentration Ranges During Surgery," 59 Anesthesiology, A379 (Sep. 1983).

Asthana et al., "Verapamil Disposition and Effect on PQ-Intervals After Buccal, Oral and Intravenous Administration," Arzneim.-Forsch./Drug Res., pp. 498-502 (1984).

Derbyshire et al., "Non-Parenteral Postoperative Analgesia," Anesthesia 39, pp. 324-328 (1984).

DeBoer et al., "Drug Absorption by Sublingual and Rectal Routes," 56 British Journal of Anaesthesiology 69 (1984).

(List continued on next page.)

OTHER PUBLICATIONS

Stanley et al., "The Effect of Population Habits on Side Effects and Narcotic Requirements During High-Dose Fentanyl Anaesthesia," 31 Can Anaesth Soc. J. 398 (1984).

Bailey et al., "Anesthetic Induction with Fentanyl," 64 Anesth Analg 48 (1985).

Stanley et al., "Management of Pain and Pain-Related Problems in the Critically Ill Patient," in Critical Care, State of the Art, vol. 6 (1985).

Huttel et al., "Sublingual Flunitrazepam for Premedication," Acta Anaesthesiol Scand. 29, pp. 209–211 (1985).

Risbo et al., "Sublingual Buprenorphine for Premedication and Postoperative Pain Relief in Orthopedic Surgery," Acta Anaesthesiol Scand. 29, pp. 180–182 (1985).

Bell et al., "Buccal Morphine—A New Route for Analgesia?" The Lancet 71 (1985).

Berry, "Premedication and Induction of the Difficult Child" (n.d.).

John F. Ryan, "Premedication, Induction and Parents," Newsletter Boston, Massachusetts (n.d.).

"Sublimize (Fentanyl) as the Citrate Injection: Product Information" (n.d.).

Stanley, "Computer Control of Intravenous Anesthesia," 423.

Schechter et al., "Status of Pediatric Pain Control: A Comparison of Hospital Analgesic Usage in Children and Adults," 77 Pediatrics 11 (1986).

Prys-Roberts et al., "Pharmacokinetics of Anaesthesia," Preface.

Bailey et al., "Pharmacology of Intravenous Narcotic Anesthetics," in Anesthesia 2nd ed. (Miller ed. 1986).

Su, "Intranasal Delivery of Peptides and Proteins," Pharmacy International (Jan. 1986).

Rothschild, "Are Sick Kids Treated Properly for Pain?", USA Today, Jan. 28, 1986.

Forbes et al., "2% Rectal Methohexital for Induction of Anesthesia in Children," vol. 65 Anesthesiology No. 3, (Sep. 1986).

Newspaper Article Entitled "Insulin Shots May Soon be Replaced by a Nasal Spray," Friday, Sep. 26, 1986, (UPI).

"New Drugs/Drug News", Hospital Therapy, pp. 9, 10, and 15 (Nov. 1986).

Davis, "Parenteral Therapy Techniques-Abstracts", Hospital Pharmacy, vol. 21, pp. 1171–1178 (Dec. 1986).

"Personalized Dosing and Effective Drugs Can Control Emesis," Pharmacy Practice News, p. 11 (Mar. 1987).

"Administration of Drugs by The Buccal Route," The Lancet, pp. 666–667 (Mar. 21, 1987).

Lee "Ophthalmic Delivery of Peptides and Proteins," Pharmaceutical Technology, pp. 26–38 (Apr. 1987).

Mecklenburg, "Insulin Pump Therapy 1987", Practical Diabetology, vol. 6, No. 2, pp. 1–7 (Mar./Apr. 1987).

Grover et al. "Low-Dose Intranasal Nitroglycerine Attenuates Pressor Response," 66 Anesthesiology, p. 722 (1987).

Oyama, Opioids in Anesthesia, Chapter 13: "Effects of Intrathecal and Epidural Morphine on Endocrine Function".

McLeskey, Opioids in Anesthesia, Chapter 20: "Continuous-Infusion Alfentanil For Surgical Anethesia".

Kitahata, Opioids in Anesthesia, Chapter 28: "Intrathecal And Epidural Short-Acting Narcoctics".

COMPOSITIONS AND METHODS OF MANUFACTURE OF COMPRESSED POWDER MEDICAMENTS

RELATED APPLICATION

This application is a continuation-in-part application of copending application Ser. No. 729,301, filed May 1, 1985, in the names of the inventors hereof, and entitled "METHODS AND COMPOSITIONS FOR NONINVASIVE ADMINISTRATION OF SEDATIVES, ANALGESICS, AND ANESTHETICS," now U.S. Pat. No. 4,671,953 which issued June 9, 1987. That application is incorporated herein by specific reference.

BACKGROUND

1. The Field of the Invention

The present invention relates to compositions and methods of manufacture of compressed powder matrixes for medicaments used in the transmucosal delivery of the medicaments. More particularly, the present invention is directed to compositions, and methods and apparatus for producing such compositions, for noninvasive administration of precise amounts of medicaments through the mucosal tissues of the mouth, pharynx, and esophagus.

2. The Background of the Invention

Recently, numerous advancements have taken place in the field of pharmacology with respect to the administration of drugs to treat various conditions. Despite the tremendous advancements in the field, however, drugs continue to be administered using substantially the same techniques that have been used for many decades. The vast majority of pharmaceutical agents continue to be administered either orally or by injection. Nevertheless, it is frequently found in the art that neither of these administration routes are effective in all cases, and both administration routes suffer from several disadvantages.

Oral administration is probably the most prevalent method of administering pharmacological medicaments. The medicament is generally incorporated into a tablet, capsule, or a liquid base, and then swallowed. The oral administration modality is often preferred because of its convenience. In addition, oral administration is generally nonthreatening, painless, and simple to accomplish for most patients.

Nevertheless, oral administration of drugs suffers from several disadvantages. One disadvantage is that pediatric and geriatric patients frequently have difficulty swallowing pills, and such patients often refuse to cooperate in swallowing a liquid medication. In addition, for many medicaments, the act of swallowing the medicament increases gastric volume and the likelihood of nausea and vomiting; this is a particularly dangerous condition for patients prior to anesthesia.

A further problem with oral administration is that the rate of absorption of the drug into the bloodstream after swallowing varies from patient to patient. The absorption of the drug is dependent upon the movement of the drug from the stomach to the small and large intestines and the effects of secretions from these organs. Anxiety and stress can dramatically reduce these movements and secretions, prevent or reduce the final effects of the drug, and delay onset of the drug's effects.

Most significant is the fact that there is normally a substantial delay between the time of oral administration and the time that the therapeutic effect of the drug begins. As mentioned above, the drug must pass through the gastrointestinal system in order to enter the bloodstream; this typically takes forty-five minutes or longer. As mentioned above, anxiety and stress often increase this delay.

For many applications, such as premedication before surgery or where immediate relief from pain or a serious medical condition or immediate effectiveness of the drug is required, this delay is unacceptable. In modern outpatient units and operating rooms where rapid turnover of patients is essential for cost containment, extensive delays in the action of a drug are simply unacceptable.

An additional disadvantage of oral administration is that many drugs, particularly drugs with central nervous system ("CNS") or cardiovascular action, are almost immediately metabolized. The veins from the stomach and the small and large intestines pass directly through the liver. Thus, drugs entering the bloodstream must first pass through the liver before distribution into the general blood circulation. More than sixty percent of most drugs (and essentially one hundred percent of certain drugs) are removed from the patient's bloodstream during this "first pass" through the liver. The result is that oral administration is impractical for many drugs, particularly most central nervous system and cardiovascular-acting drugs that are used in critical care situations, as a premedication prior to surgery, or for the induction of anesthesia.

Further, additional stress is placed on the liver as it removes the excess drug from the bloodstream. This is particularly severe if the cardiovascular or renal vascular treatment has been occurring over an extended period of time. The liver may become overloaded with the drug's metabolite which then must be excreted in the patient's urine. As a result, there is an increased risk of hepatic or renal disorders.

Another difficulty encountered in administering drugs orally is that dosages are prepared or determined for use with an "average" patient. Most drugs have widely varying effects on different patients. These effects depend upon patient habits, subtle genetic differences between patients, blood volumes, age, and numerous other known and unknown factors. Introducing a bolus of drug orally does not provide the ability to control the precise dose needed to obtain the desired effect, rather the dose is estimated in order to produce an average effect in an average patient. The result may be underdosing or overdosing a particular patient.

Underdosing a patient because of a low susceptibility to the drug fails to evoke the response sought by the physician. Overdosing the patient can result in dangerous depression of vital body functions, especially the heart and lungs. This can cause prolonged respiratory depression (necessitating mechanical ventilation after surgery), cardiac depression, and cardiac arrest.

In order to avoid some of the disadvantages of oral administration, injection is frequently used. Injecting a drug (generally intravenously or intramuscularly), results in rapid entry of the drug into the patient's bloodstream. In addition, this type of delivery avoids the removal of large quantities of the drug by the patient's liver. The drug instead becomes rapidly distributed to various portions of the patient's body before exposure to the liver.

Most patients, particularly children and geriatric adults, have an aversion to injections. In some patients, this aversion may be so pronounced as to make the use of injections a serious concern. Since intense psychological stress can exacerbate a patient's debilitated condition, it sometimes becomes undesirable to use injections where the patient is seriously ill or suffers from a debilitating condition or injury.

In addition, individual variations in susceptibility in the metabolism of various drugs (particularly drugs with central nervous system activity) are even more profound when utilizing the injection route. In order to prevent overdosing, it is the practice to inject a patient with a lower than average dose and then supplement the dose with additional injections as necessary. This "titration" makes necessary the use of repeated injections, which in turn greatly increases stress on the patient. Again, a precise dose cannot be administered to produce a precise effect because the patient's response varies widely depending on the specific characteristics of the specific patient.

One common approach to preparing a patient for surgery is to orally administer a sedative or anxiolytic. Although quick onset of sedation or anxiolysis has not always been a critical factor, it is more so now. Changing practices, including the increased use of outpatient units for day surgery and the pressures for cost containment in modern medicine, dictate rapid onset of action and the use of an absolutely ideal dose in order to avoid increased costs of caring for patients with delayed recovery secondary to slightly overdosing with anesthesia. Oral administration of premedication drugs with central nervous system activity (which cause a rapid onset of sedation and anxiolysis without producing excessive sedation) is difficult to accomplish.

Some investigators have suggested that it may be possible to administer medication through the buccal mucosa of the cheek pouch or by sublingual administration. See, copending application Ser. No. 729,301, filed May 1, 1985, in the name of the inventors hereof, and entitled "METHODS AND COMPOSITIONS FOR NONINVASIVE ADMINISTRATION OF SEDATIVES, ANALGESICS, AND ANESTHETICS." Such administration through the mucosal tissues of the mouth, pharynx, and esophagus of therapeutic drugs possesses a distinct usefulness. Administration of drugs by this route does not expose the drug to the gastric and intestinal digestive juices. In addition, the drugs largely bypass the liver on the first pass through the body, thereby avoiding additional metabolism and/or inactivation of the drug.

Generally the drugs which are administered by any of the methods described above have an unpleasant taste. As a result, in order to allow for buccal or sublingual administration through the oral mucosal tissues, it is also necessary to incorporate the drug into some type of pleasant tasting mass, such as a "candy" matrix.

In the manufacture of medicated candy products by existing methods, the therapeutic agent is added to a molten candy mass. The resultant mixture is then thoroughly mixed to ensure proper distribution of the drug within the molten candy mass. The mixture is then poured while still molten and allowed to solidify into a semi-solid mass. Alternatively, the hot candy mass may be poured into molds, the size and shape of which may be determined as desired.

For effective application of the drug, the final candy product must contain the drug uniformly distributed throughout in order to ensure uniform levels of medication. Alternatively, for some applications, varying concentrations within known and controlled ranges may be desired to vary the rate of drug administration. Difficulties are encountered in attempting to blend solid drugs in a uniform or otherwise carefully controlled manner. Many drugs are insoluble, or only partially soluble, in one or more of the ingredients of the hard candy base. Thus, the resultant product is often found to be lacking in uniform distribution of the drug.

In addition, it is often found that when the temperature of the candy mass is increased in order to enable a more uniform distribution (generally to a temperature above approximately 230° C.), considerable decomposition of the drug takes place. While the extent of decomposition may vary, high temperatures are generally undesirable in the handling and processing of medications. Thus, the process of formation of the candy product may itself degrade and/or inactivate the therapeutic agent.

Furthermore, many presently available medicated candy lozenges tend to crumble when placed in the mouth. As a result, uniform release of the drug into the mucosal tissues does not take place. Rather, the crumbled lozenge is mostly chewed, and swallowed, and the drug enters the bloodstream through the stomach and intestines as described above. Thus, it will be appreciated that candy lozenges have very definite limitations for use in the administration of a drug through the oral mucosal tissues. As a result, lozenges have not been used to administer potent, fast-acting drugs, such as drugs that affect the central nervous system, the cardiovascular system, or the renal vascular system.

While the administration of certain drugs through the oral mucosal tissues has shown promise, development of a fully acceptable method for producing a medication in a desirable form and administering the medication has been elusive. It has not been possible to develop an acceptable candy product for use with most drugs without heating the product to the point where degradation will be expected.

It should also be noted that pH conditions within the mouth tend to adversely affect the administration of certain drugs by the mucosal administration route. It has been found in the art that administration of drugs through the mucosal tissues occurs best when the drug is in the non-ionized form. Variations in pH affect drastically the percentage of the drug which is non-ionized at a particular point in time. As a result, the pH conditions within the mouth limit the effectiveness of certain drugs administered buccally or sublingually in that those conditions cause the drug to exist in the ionized form which is largely unavailable for transfer across the mucosal tissues.

In view of the foregoing, it would be an important advancement in the art of administering potent, fast-acting drugs, if suitable methods and compositions provided a precise dosage to a precise effect in every patient. It would be a related advancement in the art to provide such methods and compositions which avoided the disadvantages of overdosing, underdosing, and the immediate metabolism encountered in the "first pass effect," yet did not involve injection by needle into the patient.

It would be a further significant advancement in the art to provide methods and compositions for incorporating drugs (including insoluble drugs) into a soluble matrix without heating the mixture to the point that degradation occurs. It would be a related advancement in the art to provide such a method which provided the capability of uniformly incorporating insoluble drugs into the soluble matrix. It would be another advancement to provide methods of controlling pH during mucosal delivery of a drug such that the drugs exist primarily in the non-ionized form.

Such compositions and methods of manufacture are disclosed and claimed herein.

BRIEF SUMMARY AND OBJECTS OF THE INVENTION

The present invention relates to compositions and methods of manufacture for producing a medicament composition for use in administering potent, fast-acting drugs transmucosally. Furthermore, the present invention relates to such compositions and methods which are useful in administering drugs in a dose-to-effect manner such that sufficient drug is administered to produce precisely the desired effect. The invention also relates to a manufacturing technique that enables a therapeutic agent to be incorporated into a flavored confectionary base and to compress or otherwise attach the solid confectionary mixture onto an appliance or holder. In use, the present invention provides for the administration of drugs through the mucosal tissue of the mouth, pharynx, and esophagus, thereby avoiding the problems of both injection and oral administration.

Employing the present invention, the drug may be introduced into the patient's bloodstream almost as fast as through injection, and much faster than using the oral administration route, while avoiding the negative aspects of both methods.

The present invention achieves these advantages by incorporating the drug into a soluble candy matrix. The soluble candy-drug mixture, in the form of a compressed powder lollipop, can be used to administer drugs in a dose-to-effect manner, or until the precise desired effect is achieved. The lollipop can then be removed from the patient's mouth.

The methods of the present invention also provide for a compressed powder composition which overcomes many of the limitations previously encountered in forming a medicated lozenge. The present invention teaches the combination of dry powdered ingredients by geometric dilution. That is, the two smallest ingredients by weight are first thoroughly mixed, then the next smallest ingredient or ingredients by weight equal to the weight of the previous ingredients is added and is thoroughly mixed with the existing mixture. This procedure is repeated until all of the components, including the desired therapeutic agents, are fully combined.

After mixing, the mixture is then compressed under high pressure to form an integral candy product. Specific confectionary components are combined in order for the mixture to form an integral solid mass. These components may include, for example, compressible confectioner's sugar and maltodextrin.

This procedure overcomes many of the problems of the prior art. According to the present invention, insoluble drugs can be added to the matrix without the necessity of attempting to dissolve the drug. In addition, the high temperatures, which are generally required to form a molten candy matrix and which will cause degradation of the drug, are avoided using the present invention. Therefore, even drugs with melting points below approximately 130° C. to 140° C. or those drugs which can experience decomposition below their melting points, can be incorporated into a soluble matrix.

A further advantage of the present invention is that flavoring problems are overcome. Flexibility in adding flavors is provided in that solubility of the components is not required in order to incorporate any particular flavor into the matrix. Thus, flavorings, drugs, and other components (which may be insoluble in liquid form) are easily mixed when they exist as a dry powder.

Buffers and other types of pH and pKa control can also be added simultaneously in order to provide for maximum drug efficiency. It will be appreciated that drugs in the non-ionized form are more readily transported across the mucosal membrane. Therefore, if pH (and corresponding pKa) conditions can be adjusted to maximize the percentage of non-ionized drug available, the effectiveness of the drug is maximized.

Various lollipop configurations are also possible employing the present invention. For example, layers of drug may be interspersed between layers of candy. Since the present invention teaches the use of solid powders, any desired type of mold can be used for the compression formation of the lollipop.

It may also be desirable to incorporate a stick into the candy matrix as the matrix is being compressed. Alternatively, the stick may be glued to the candy matrix by a confectioner's glue once the lollipop is formed. The stick provides for easy removal of the lollipop from the mouth of the patient once the desired effect has been achieved. This is a substantial improvement over existing methods of administering drugs through the mucosal tissues of the mouth.

The present invention also provides the advantage of controlling the dissolution rate of the composition once it is administered to a patient. This can be accomplished in two ways. First, the dissolution rate may be modified chemically by including a hydrophobic agent (such as calcium stearate) to slow dissolution or lactose to enhance dissolution. Dissolution may also be controlled by the extent to which the mixture is mechanically compacted.

A drug administered through the oral mucosal tissues from such a compressed powder matrix within the scope of the present invention will quickly enter the patient's bloodstream through the veins which serve these tissues. Appropriate monitoring of the patient's reaction to the drugs which has an observable or monitorable effect (such as a drug effecting the central nervous, cardiovascular, or renal vascular systems) will indicate when the drug has evoked a suitable response. The lollipop may then be removed, or its rate of consumption may be modified in order to maintain the desired effect.

It will be appreciated that the ever present risk of overdosing a patient is substantially minimized through the use of the present invention. The rate at which the drug is to be absorbed by the body can be varied by varying the rate the lollipop dissolves. This can be accomplished by varying the rigor with which the patient sucks on the lollipop. It can also be accomplished by varying the extent to which the lollipop is compressed during formation or by adding certain agents which reduce the solubility of the compressed powder matrix.

According to the present invention, the drug dose is given over a period of time rather than all at once, and the administration rate can be adjusted if it appears to be necessary. Once a sufficient drug response has been achieved, the patient can simply stop sucking on the lollipop or the physician can easily remove the lollipop from the patient's mouth.

It is, therefore, a primary object of the present invention to provide methods of manufacture and compositions in order to accomplish the non-invasive administration of a drug to a patient in order to rapidly induce a desired central nervous system effect.

It is another object of the present invention to provide methods of manufacture for forming a drug-containing compressed powder matrix, which methods avoid degradation of the drug, overcome problems related to insolubility of the various components in the candy matrix, and provide a product which is not likely to crumble in the patient's mouth.

It is another object of the present invention to provide compositions which allow for precise control of the dosage and effect of the drug to be administered.

These and other objects and features of the present invention will become more fully apparent from the following description and appended claims taken in conjunction with the accompanying drawings.

DETAILED DESCRIPTION OF THE PREFERRED EMBODIMENTS

1. General Discussion

Figure 1:
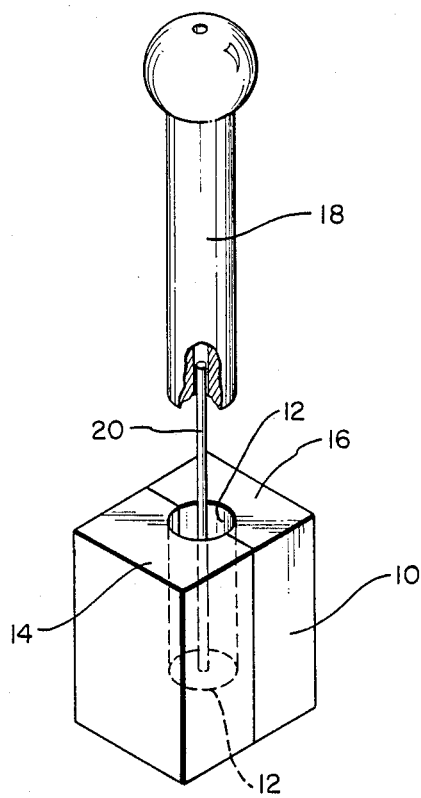
FIG. 1 is a perspective view of a mold for forming the candy-drug matrix along with an associated ram.

The present invention is related to methods of manufacture and compositions which facilitate the transmucosal delivery of a medication. Simply stated, the present invention relates to a lollipop, or similar type of composition, which contains a therapeutic drug. The drug is delivered to the patient through the mucosal tissues of the mouth, pharynx, and esophagus as the patient sucks on the drug-containing lollipop.

This particular method of delivery overcomes several of the limitations encountered in the delivery of drugs either orally or by injection. One of the primary advantages of the present invention is the ability to introduce drugs to a patient in a "dose-to-effect" manner. The drug is given to the patient until the precisely desired effect is obtained; this is in distinction to prior art methods where a predetermined quantity of the drug is introduced to the patient. Once the desired effect is obtained, the patient or the medical professional simply removes the lollipop from the patient's mouth.

The present invention discloses a method of producing a lollipop containing one or more therapeutic agents. The present invention overcomes many of the problems encountered generally in incorporating drugs into a confection. For example, the present invention teaches the mixing of solid powders at room temperature, as opposed to liquid components at elevated temperatures. The degradation of drugs, which often occurs at the elevated temperatures needed to produce a molten candy mass, is thereby avoided. This facilitates use of drugs having melting points in the 130° C.–140° C. range and below, or those drugs which can experience decomposition below their melting points.

In addition, because solid powders are combined together, constituents which may be chemically incompatible when in a heated solution or suspension can be mixed. In forming medicated confections by known methods, severe problems are encountered in that the medication, flavorings, and other components may be insoluble when placed in the same liquid environment. In addition, problems of chemical imcompatibility between ingredients is eliminated in the present invention.

Once the desired constituents are thoroughly mixed, they are compressed into a solid mass under high pressure. Typically, compressive forces in the range from approximately 2,000 Newtons to approximately 5,000 Newtons are preferred. As a result, the compressed powdered matrix is held together by physical means rather than by chemical means. The extent of the compressive forces can be modified to vary the rate that the lollipop will dissolve in a patient's mouth. The greater the compressive forces that form the mixture, the slower the dissolution of the compressed powder matrix in the mouth.

The rate of the dissolution of the lollipop can also be controlled chemically. For example, the rate of dissolution can be reduced adding hydrophobic agents such as calcium stearate. Alternatively, dissolution can be increased by adding hydrophilic agents, such as lactose.

According to the present invention, the compressed powder matrix is attached to a holder, such as a stick to form a lollipop. Attaching the compressed powder matrix to a holder facilitates the administering of precise dosages. Once a particular effect is induced, the lollipop can be withdrawn using the holder as described above. In addition, a compressed solid mass containing a drug having complex disagreeable flavor characteristics require multiple ingredients to be added in order to provide a significant bulk to overcome the disagreeable flavor characteristics; hence, a mechanical support system such as a holder is necessary.

The attachment of the confection to a holder may be made by compressing the stick into the powder matrix as the lollipop is being formed. Alternatively, the stick may be glued to the candy matrix by confectioner's glue or some other appropriate adhesive once the matrix is formed. In the alternative, as will be discussed below, a lollipop may be assembled immediately prior to use by sliding disks of drug and candy onto an appropriately configured holder.

It will be appreciated that compression or attachment of the drug-containing confection onto a holder can facilitate the transmucosal absorption of a variety of therapeutic agents. Attachment to a holder also facilitates verifiable transfer of the medication to the patient. The holder provides a convenient point of reference concerning quantities of drug administered at any particular point in time; it is easy to determine how much of the lollipop has been dissolved in the patient's mouth.

Localization of effects by agents such as local anesthetic agents, antiplaque agents, local antipruitic agents, local antisecretory agents, and local antifungal agents can also be accomplished according to the present invention. Immediate systemic effects from central nervous system-acting drugs (such as sedation, anxiolysis, analgesia, amnesia, and anesthesia), cardiovascular-acting agents (such as antihypertensives and and antianginal drugs), renal vascular-acting agents, and numerous other therapeutic agents can also be accomplished by employing the present invention.

Placing a drug dosage onto a holder also facilitates the temporary removal of medication for inspection or the reduction of the effect when necessary. Unlike administration of drugs orally or even sublingually, the present composition can easily be removed to assess the effect induced at any particular time. When a pill or lozenge is used, removal from the patient's mouth at an intermediate stage to assess effect is generally impractical, if not impossible.

Compressed powder matrixes attached to a holder can also avoid aspiration of the confection. One major problem with existing lozenges and the like is their tendency to crumble. Once the lozenge crumbles, controlled transmucosal delivery is impossible. In addition, there is some possibility that the patient will choke on the pieces of lozenge.

The present invention provides the capability of providing a good tasting medication. With many drugs, it has previously been impossible to provide a good tasting medicine because of the extreme bitterness or other unpleasant taste of many drugs. Using the present invention, favorable taste characteristics can be accomplished by adding various flavors, sweeteners, and the like to form an ideal mix of products. Since the components are combined as solids, problems associated with combining flavoring components insoluble in a molten candy mass are avoided.

It is also important to note that it has been found that it is possible, according to the present invention, to use the free acid form of certain drugs and to buffer those drugs such that extremes in pH, and resulting bad taste, are avoided.

2. Methods of Manufacture

In order to prepare a desirable drug-confection mixture for formation into a lollipop, it is generally necessary to combine several general types of components. These components include the types of components used to prepare typical confections, the desired drug, and other chemically active ingredients such as buffers and the like. The types of components involved generally fall into the following categories:

(1) flavorings,
(2) sweeteners,
(3) flavor enhancers,
(4) releasing agents,
(5) buffers, and
(6) one or more therapeutic agents.

As mentioned above, it is preferred that these components each be provided in a powder, in order to facilitate the mixing and compression steps. This provides for convenient combination of the ingredients, even if they happen to be insoluble or otherwise chemically incompatible. All the incipients or inactive ingredients should be on the GRAS list ("generally regarded as safe").

A wide range of flavors are available for preparing good tasting and desirable medications within the scope of the present invention. These are required in order to mask the unpleasant taste of the drug. Flavorings may be combined, as desired, to produce a particular flavor mix which is compatible with a particular medication. Some of the confectioner's flavorings which have been used in the context of the present invention include artificial vanilla, vanilla cream, mint, cherry, spearmint, grape, coconut, chocolate, menthol, licorice, lemon, and butterscotch.

Each of these flavorings is obtainable in a concentrated powder form. Other flavorings known in the confectionary arts may also be acceptable because of the ease of combining the ingredients of the present invention. Any number of flavorings may be combined in any desired ratio in order to produce the specific desired taste characteristics required for any particular application. For example, flavor combinations may be varied in order to be compatible with the flavor characteristics of any specific drug.

In order to produce a desirable color for the end product, artificial colorings may also be added to the composition. The flavorings described above are generally a white powder, as are the other major components. Therefore, additional coloring is necessary if a colored end product is desired. Coloring may also be important as a code to indicate the type and concentration of drug contained within a particular lollipop. Any type of color known to be "generally regarded as safe" ("GRAS"), and thus generally used in the confectionary trade, may be used to provide coloring to the product.

In order to provide a good tasting medication, it is necessary to add sweeteners to the composition. Sweeteners which are presently preferred include aspartame (NutraSweet ®) and compressible confectioner's sugar. Other sweeteners, such as fructose, may also be acceptable for use within the scope of the present invention. Again, it is desired that a sweetner or combination of sweeteners be obtained which is compatible with the drug and the other components such that a good tasting confection is produced.

Maltodextrin may also be added to provide a better tasting composition. Maltodextrin is generally employed in order to dissipate unpleasant flavors (such as the bitter taste of most drugs) within the composition. In addition, maltodextrin is a highly compressible powder which facilitates the formation of the final lollipop product.

For some applications, it may be desirable to add a flavor enhancer to the composition in order to achieve a good tasting product. Flavor enhancers provide a more pleasant sensation in the patient's mouth during consumption of the lollipop. Flavor enhancers within the scope of the present invention include materials such as ribotide (a nucleotide) and monosodium glutamate ("msg").

In certain medications, it may also be desirable to add a lubricating agent in order to release the lollipop from the mold. Such agents may also provide a certain amount of waterproofing. As mentioned above, the rate of dissolution of the lollipop within the patient's mouth may be controlled chemically, as well as physically, through the extent of compression of the composition. These lubricating or releasing agents may include substances such as compritol 888, calcium stearate, and sodium stearate. Compritol 888 is a trade name for glyceryl behenate. These agents may enhance dissolution or they may inhibit dissolution as necessary.

As will be discussed in more detail below, it may also be desirable to buffer the composition. Buffers provide the ability to place the medication in the mouth in a favorable pH environment for passage across the mucosal tissues of the mouth, pharynx, and esophagus. Buffers incorporated within the composition can be used to affect a pH change in the salival environment of the mouth in order to favor the existence of a non-ionized form of the active ingredient or drug which more readily moves through the mucosal tissues.

In addition, appropriate pH adjustment can aid in producing a more palatable product with drugs which are either severely acidic (and thus sour) or severely basic (and thus bitter). As a result, a buffer system such as citric acid/sodium citrate has been found to be desirable for addition into the soluble compressed powder matrix.

It will be appreciated that miscellaneous other agents such as lactose, to provide filling and bulk, may also be desirable. Other filling and bulking agents of the type known in the art may also be used.

Added to the confectionary matrix described above will be the appropriate therapeutic agent or drug. As will be discussed in more detail below, various types of drugs are easily incorporated into this type of matrix. These include agents which affect the central nervous system, the cardiovascular system, or the renal vascular system.

A typical lollipop within the scope of the present invention may include the following ingredients in order to make 20 dosage forms of 2000 milligrams (2 grams) each:

| Ingredient | % | grams |
|---|---|---|
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| | 23% | 4.6 grams |
| generic active agent X% (about 0.05%) | | |
| maltodextrin $\frac{100\% - (23\% + \text{active agent }\%)}{3} \times 2$ | | |
| compressible sugar $\frac{100\% - (23\% + \text{active agent }\%)}{3}$ | | |

Appropriate changes in flavoring ingredients can be made in this formula to mask or optimize flavor perception in order to achieve ultimate acceptance of the dosage formed by the desired patient group, be it adult, juvenile, pediatric, or neonate.

Each of the components is mixed with the other components in dry form to produce the compositions of the present invention. It is presently preferred to use the method of geometric dilution in mixing the various components. Using this method, the two smallest ingredients by weight (as a proportion of the final product) are first mixed together thoroughly.

When complete mixing has been obtained between those two components, the next smallest ingredient or ingredients by weight equal to the weight of the previous ingredients is added and mixed thoroughly with the existing mixture. This procedure is repeated until all of the components are added to the mix and mixed thoroughly with all other components.

Geometric dilution provides for complete and thorough mixing of all of the components. Using the method described above, there is little chance for incomplete mixing and uneven distribution of components throughout the mix. It will be recognized that this is an advancement over the art in that existing methods may result in incomplete mixing because of the insolubility of the products.

Once complete mixing is accomplished, the mixture is compressed under relatively high forces to provide a coherent dosage. Compressive forces in the range of from approximately 2,000 Newtons to approximately 5,000 Newtons are presently preferred, however, any force which is sufficient to compress the ingredients into a coherent, integrated mass could be used.

When employing the present invention, there is no need to heat the mixture to a molten mass as has been the practice in the past in forming drug-containing confections. As a result, heat degradation of the drug component is avoided while good mixing and a uniform product are provided.

The confectionary mass may be attached to a holder such as a stick or other similar type of holder. The holder may be glued to the confection by confectioner's glue. Alternatively, the holder may be compressed into the lollipop by the compressive forces described above.

The figures illustrate several methods of forming the mass of confection, as well as methods of attaching the holder. FIG. 1 discloses a mold block 10. The interior of mold block 10 includes a cavity 12 formed in any desired shape so that the ingredients described above can be compressed sufficiently to form an appropriately shaped dosage. Mold block 10 may comprise two separate halves 14 and 16. Each half of the mold block 10 can be removed in order to remove the confection once it is sufficiently compressed.

Also illustrated in FIG. 1 is ram 18. Ram 18 is configured so that it fits into the cavity 12 and compresses the confection into the base of cavity 12. Ram 18 may have a hole disposed through its interior in order to accommodate stick 20. Thus, stick 20 can be placed into the mass of confection prior to compression. Ram 18 will then compress the confection tightly around stick 20. Following compression of the confection, the stick is securely bound in place.

Figure 2:
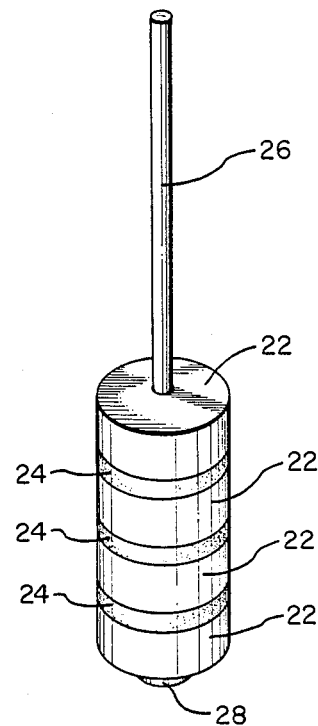
FIG. 2 is a perspective view of one embodiment of a lollipop within the scope of the present invention.

FIG. 2 discloses an additional embodiment of the confection of the present invention. The confection illustrated in FIG. 2 has alternating layers of confectionary mass 22 and a drug mass 24. Each alternating segment is disk-shaped with the width of the disk being varied according to particular needs. Disks 22 and 24 easily slide over stick 26 and seat against button 28. Thus, the method of assembly of the confection can be adapted to produce various dosages to fit varying circumstances. Indeed, the patient himself may be capable of assembling an appropriate confection and varying the content of the medicament to correspond to his specific needs at any particular time.

Figure 3:
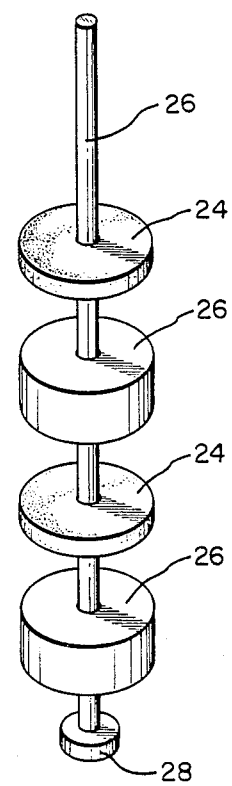
FIG. 3 is an exploded plan view of the embodiment of the lollipop shown in FIG. 2.

FIG. 3 illustrates the method of assembling the embodiment of the invention as illustrated in FIG. 2. In FIG. 3, the drug disks 24 and confection disk 22 are spaced apart along stick 26. As can be appreciated from FIG. 3, disks 22 and 24 will slide onto stick 26 and will seat against button 28. The number of disks and the composition of these disks can be easily varied to meet particular patient needs.

Stick 26 may take various shapes. For example, it may be desirable for stick 26 to be oval or triangular in cross section. This would prevent disks 24 and 26 from turning on the stick. In addition, an additional sleeve (not shown) may be positioned over the exposed portion of the stick with a catch that engages stick 26 so that disks 24 and 26 are locked in place.

Figure 4:
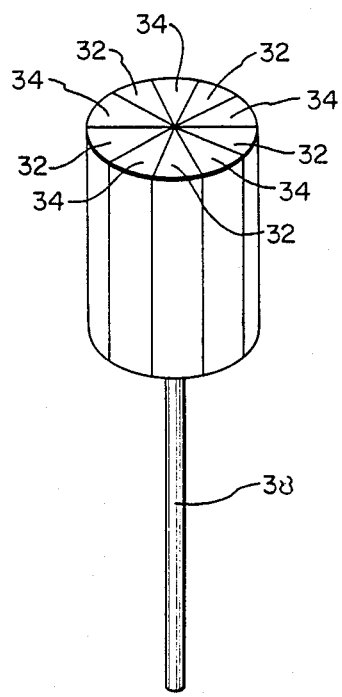
FIG. 4 is a perspective view of an alternative embodiment of the lollipop of the present invention.

FIG. 4 illustrates a further embodiment of a composition within the scope of the present invention. In FIG. 4, the drug and confection are divided laterally along the cylindrical mass of the confection. Thus, pieshaped segments of drug 32 and confection 34 are pressed together around stick 30. As illustrated in FIG. 4, drug segments 32 and confection segments 34 may alternate around a periphery of the confectionary mass. Alternatively, the spacing of the segments may be varied to provide other appropriate levels of drug dosage.

Figure 5:
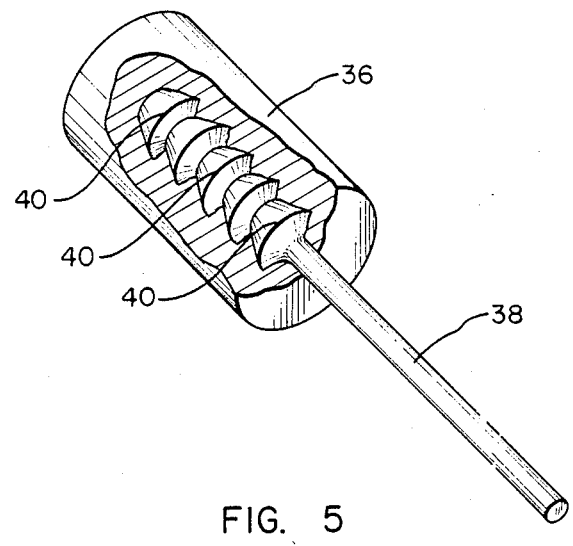
FIG. 5 is a cutaway plan view of an alternative embodiment of the lollipop of the present invention illustrating one method of attachment of the stick to the candy matrix.

FIG. 5 illustrates an alternate method of attachment between the confectionary mass 36 and the stick 38. Stick 38 illustrated in FIG. 5 is constructed with a plurality of protrusions 40. Protrusions 40 extend toward the exposed portion of the handle such that they prevent the confection from sliding off the handle. Thus, when the confectionary mass 36 is compressed around stick 38, the mass is securely bound to the stick.

It can be seen, therefore, that the present invention provides a great deal of flexibility in the construction of an appropriate drug-containing confection. The quantity of drug contained in any confection can be varied within wide ranges. In addition, various methods of attachment of the confection to the stick are available in order to provide a wide range of flexibility.

3. Control of pH and pKa

It is well known that most drugs are weak acids or weak bases and are present in solution in both the non-ionized and ionized forms. It has been found that the non-ionized portion of the drug is usually lipid soluble and can readily diffuse across the cell membrane. The ionized portion, conversely, is lipid insoluble and is often unable to penetrate the lipid membrane of the cell. Furthermore, the ionized drug is often unable to cross the cell membrane pores because of its positive or negative charge. As a result, drugs in the ionized form are generally inefficient in producing a drug effect on the central nervous, cardiovascular, and renal vascular systems.

Whether a drug exists in the ionized or non-ionized form is largely dependent upon its pKa, and correspondingly on the pH of the solution. The present invention provides the unique ability to control the pH of the solution and thus the pKa of the drug.

Ingredients of the lollipop or other dosage form can be designed to impart sufficient change in the pH of the saliva within the mouth such that the concentration of the non-ionized drug is increased. When the percentage of non-ionized drug is increased, transmucosal absorption of the drug is correspondingly increased. Therefore, by influencing the salival pH environment, it is possible to greatly improve the extent and rapidity of actual drug absorption, and therefore, the initial onset of the effect of the drug. Adding pH buffering systems (such as citric acid/sodium citrate) into the lollipop dosage can greatly facilitate delivery of the drug in the non-ionized (lipid soluble) form.

It is often desirable for the pKa to range from approximately 5 to approximately 8 in order to maximize drug delivery. pKa is the dissociation constant, which is generally defined as the pH at which a given acid or base is 50% ionized and 50% non-ionized. pKa can be calculated from pH, if the concentrations of the charged and uncharged species are known, using the well-known Henderson-Hasselbach equation if concentrations of the changed and unchanged species are known. The Henderson-Hasselbach equation is as follows:

$$pKa = pH + \log \left| \frac{A-}{HA} \right|$$

where A-/HA is the ratio of the ionized drug form ("A-") to the non-ionized drug form ("HA").

The effect on the pKa of varying pH, and thus on the non-ionized drug available, is extremely dramatic. For example, methohexital, a potent central nervous system-acting drug, has a pKa of 7.9. If at the same time the general pH of the saliva is about 7.5, these values can then be placed in the Henderson-Hasselbach equation as follows:

$$7.9 = 7.5 + \log (X) \text{ (log of the ratio of ionized to non-ionized)}$$

where X is the ratio of the ionized to the non-ionized drug form. Solving this calculation indicates that under typical conditions in the mouth, 60% of the methohexital available would exist in the non-ionized form. As was mentioned above, the non-ionized drug form is the primary form that is transported across the lipid cell membrane.

In the event that the salival pH is buffered down to approximately 6.7, the pKa changes dramatically. This results in a corresponding dramatic change in the amount of drug available. Under these conditions, 94% of the drug available exists in the non-ionized form.

Comparing the pKa produced under the two sets of pH conditions described above, it can be seen that dramatic changes occur. Changing the pH from 7.5 to 6.7 produces more than a 50% improvement in the concentration of non-ionized drug available for delivery across the lipid membrane. This results directly in a dramatic improvement in drug delivery across the cell membranes in the mouth and a corresponding increase in the effectiveness of the drug administered.

Changes in pH such as those discussed above can be accomplished by incorporating particular buffer systems within the confection composition. One presently preferred buffer system is a citric acid/sodium citrate system; however, other conventional buffers (such as phosphate) may also be used. By using such a buffer, dramatically better results may be achieved such that buccal drug absorption is a fully feasible and optimal delivery method.

It will be appreciated that an additional advantage of the change of the pH may be that the taste characteristics of the drug can be improved. Drugs which are very high in pH typically are very bitter in taste. As the pH drops, the taste becomes less bitter, then salty, and may eventually become sour. Flavorings can more adequately improve the taste characteristics of drugs in the lower pH ranges. As a result, in addition to improving the drug delivery, buffering pH may also improve the taste characteristics of the composition.

4. Suitable Therapeutic Agents

In order for the present invention to operate effectively, it is necessary that the therapeutic agent incorporated within the candy matrix be generally lipophilic or, in the alternative, be capable of being placed in lipophilic form by suitable adjustments in the environmental pH or other chemical modification. Thus, it is presently preferred that the drug have a pKa in the range of from approximately 6 to approximately 8.

It will be appreciated that the present invention may be used with drugs having a variety of melting points. Even low melting point drugs may be used in the present invention, whereas such drugs were difficult to incorporate into a candy matrix using known methods because of problems such as degradation of the drug. For example, methohexital, one of the presently preferred drugs for use in connection with the present invention, has a melting point of approximately 96° C. In order to incorporate methohexital into a hard candy by conventional techniques, the drug would have to be melted and there would be a risk of extensive decomposition of the active agent.

The present invention has applicability to a variety of drugs affecting the central nervous system. For example, the present invention may easily be utilized in the administration of buterophenones (such as droperidol and haloperidol); benzodiazepines (such as valium, midazolam, triazolam, oxazolam, and lorazepam); gABA stimulators (such as etomidate); barbiturates (such as pentathol, methohexital, thiamazol, pentobarbital, and hexabarbital); di-isopropylphenols drugs (such as diprivan); and other central nervous system-acting drugs such as levodopa. It will be appreciated that other drugs may also be utilized within the scope of the present invention either singly or in combination. It is important, however, that the drug be generally lipophilic, potent, and have the other general characteristics described herein.

Table 1 lists some of the CNS-acting drugs which are suitable for incorporation into the lollipop of the present invention, as well as some of the characteristics of those drugs.

Drugs having effects on the cardiovascular and renal vascular systems may also be incorporated into the compressed powder lollipop of the present invention. A few examples of such drugs are identified in Table 2.

TABLE 2

| GENERIC DRUG | CLASS/FUNCTION | MELT P. | LOLLIPOP DOSE RANGE |
|---|---|---|---|
| Bretylium | antiarrhythmic | 97° C. | 50–500 milligrams |
| Capitopril | ACE inhibitor | 87° C. | 25–75 milligrams |
| Clonidine | hypotensive agent | 130° C. | 0.1–0.5 milligrams |
| Enalapril | ACE inhibitor | 115° C. | 5–15 milligrams |
| Esmolol | hypotensive/angina | | 100–250 milligrams |
| Isosorbide | angina | 70° C. | 2.5–40 milligrams |
| Labetolol | hypotensive | 120° C. | 100–400 milligrams |
| Lidocaine | antiarrhythmic | 127° C. | 50–250 milligrams |
| Metoprolol | hypotension | 97° C. | 25–100 milligrams |
| Nadolol | hypotension | 124° C. | 40–160 milligrams |
| Nifedipin | hypotensive/angina vasodilator | 172° C. | 10–40 milligrams |
| Nitroglycerin | hypotensive/angina | 50° C. | 0.4–1.0 milligram |
| Nitroprusside | hypotensive | 90° C. | 10–50 milligrams |
| Propranolol | hypotension/angina | 96° C. | |
| Dopamine | renal vascular | 241° C. | 0.5–5 milligrams |

In addition to the foregoing, there are many other drugs which can be incorporated into the compressed powder matrix of the present invention. Exemplary of such drugs are those identified in Table 3.

TABLE 3

| Antiemetic | |
|---|---|
| Drug Generic | Dose Range |
| Benzquinamide | 25–100 milligrams |
| Meclizine | 25–100 milligrams |
| Metoclopramide | 5–20 milligrams |
| Prochlorperazine | 5–25 milligrams |
| Trimethobenzamide | 100–2500 milligrams |

| Antifungal | |
|---|---|
| Drug Generic | Dose Range |
| Clotrimazole | 10–20 milligrams |
| Nystatin | 100,000–500,000 units |

| Antiparkinson | |
|---|---|
| Drug Generic | Dose Range |
| Carbidopa | with levodopa 10–50 milligrams |
| Levodopa | 100–750 milligrams |

| Antisecretory | |
|---|---|
| Drug Generic | Dose Range |
| Sucralfate | 1–2 grams |

| Bronchodilator | |
|---|---|
| Drug Generic | Dose Range |
| Albuterol | 0.8–1.6 milligrams |
| Aminophylline | 100–500 milligrams |

TABLE 1

| GENERIC DRUG | DRUG CLASS | MELTING POINT | DOSE RANGE |
|---|---|---|---|
| methohexital | barbiturate | 92° C. | 10–500 milligrams |
| pentobarbital | barbiturate | 131° C. | 50–200 milligrams |
| thiamylal | barbiturate | 127° C. | 10–500 milligrams |
| thiopental | barbiturate | 160° C. | 50–500 milligrams |
| diazepam | benzodiazepine | 125° C. | 10–40 milligrams |
| lorazepam | benzodiazepine | 166° C. | 1–4 milligrams |
| midazolam | benzodiazepine | 158° C. | 2–25 milligrams |
| oxazepam | benzodiazepine | 205° C. | 5–40 milligrams |
| triazolam | benzodiazepine | 233° C. | 250–1000 milligrams |
| droperidol | buterphenone | 145° C. | 1–10 milligrams |
| haloperidol | buterophenone | | 0.5–10 milligrams |
| propanidid | eugenol | | |
| etomidate | GABA stimulator | 67° C. | 5–60 milligrams |
| disoprofol | — | | |
| ketamine | phencyclidine | 262° C. | 20–300 milligrams |
| diprivan | phenol | | 5–20 milligrams |

TABLE 3-continued

| | |
|---|---|
| Beclomethasone | 20-50 micrograms |
| Dyphylline | 100-400 milligrams |
| Epinephrine | 200-500 micrograms |
| Flunisolide | 25-50 micrograms |
| Isoetharine | 170-680 micrograms |
| Isoproterenol HCl | 60-260 micrograms |
| Metaproterenol | 0.65-10 milligrams |
| Oxtriphylline | 50-400 milligrams |
| Terbutaline | 2.5-10 milligrams |
| Theophylline | 50-400 milligrams |

Migraine

| Drug Generic | Dose Range |
|---|---|
| Ergotamine | 2-4 milligrams |
| Methysergide | 2-4 milligrams |
| Propranolol | 80-160 milligrams |
| Suloctidil | 200-300 milligrams |

Oxytocic

| Drug Generic | Dose Range |
|---|---|
| Ergonovine | 0.2-0.6 milligrams |
| Oxytocin | 5-20 units |

Antidiuretic

| Drug Generic | Dose Range |
|---|---|
| Desmopressin acetate | 10-50 micrograms |
| Lypressin | 7-14 micrograms |
| Vaspressin | 2.5-60 units |

Hypoglycemic

| Drug Generic | Dose Range |
|---|---|
| Insulin | 5-20 units |

When incorporating a drug into a lollipop or candy matrix within the scope of the present invention, the amount of drug used will generally differ from the amount used in more traditional injection and oral administration techniques. Depending upon the lipophilic nature of the drug, its potency, and its end use, the total concentration of the drug in the typical lollipop may contain up to 50 times the amount of drug which would typically be used in an injection. For purposes of example, Tables 1, 2, and 3 set forth presently contemplated ranges of the dosages of certain drugs which could be typically used.

A wide variety of drugs may be used within the scope of the present invention. The present invention allows drugs to be incorporated within the candy matrix which would otherwise be insoluble, unpleasant tasting, or have other undesirable characteristics. This capability is provided by the compression formation of the candy dosage.

As was mentioned above, methohexital is one presently preferred drug for use in the lollipop of the present invention. Tests were run in which methohexital lollipops were given to six volunteers. The lollipops each contained 500 milligrams of methohexital. Each patient experienced the sedative effects of the drug in a matter of minutes after beginning to suck on the lollipop. These tests indicated that the lollipop of the present invention is effective in administering methohexital in a dose-to-effect manner.

Using the methohexital lollipop described above, it was possible to produce either mild or heavy sedation or induce anesthesia. By removing the lollipop when the ideal degree of sedation was achieved, it was possible to gradually increase sedation to the desired level.

In addition, the results show that the use of oral transmucosal methohexital significantly decreases the drug dosage required to produce optimal sedation. The dosage was reduced from between 25 and 30 mg/kg when methohexital is administered rectally to between 6 and 8 mg/kg methohexital is given by way of the lollipop.

In summary, it will be appreciated that a wide variety of drugs can be used within the scope of the present invention. At the same time, several benefits are provided. Efficient delivery of the drug is facilitated while at the same time drug degradation is avoided. The drug can also be administered in a dose to effect manner so that the drug effect produced is precisely controlled.

5. Examples of the Present Invention

The following examples are given to illustrate various embodiments which have been made or may be made in accordance with the present invention. These examples are given by way of example only, and it is to be understood that the following examples are not comprehensive or exhaustive of the many types of embodiments of the present invention which can be prepared in accordance with the present invention.

EXAMPLE 1

In this example, methohexital was incorporated into a compressed dosage form. Methohexital is a known potent lipophilic drug useful as an anxiolytic, sedative and for anesthetizing a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 20% | 4.0 |
| methohexital sodium | 25% | 5.0 |
| maltodextrin | 32% | 6.4 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage forms, each containing 0.5 grams of methohexital.

EXAMPLE 2

In this example, triazolam was incorporated into a compressed dosage form. Triazolam is a known potent lipophilic drug useful as an anxiolytic, amnestic, and for sedating a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| triazolam | 0.05% | 0.01 |
| citric acid | 1% | 0.2 |

-continued

| Ingredient | % | grams |
|---|---|---|
| Ribotide | 2% | 0.4 |
| Compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 25.65% | 5.13 |
| maltodextrin | 50.3% | 10.26 |
| | 100% | 20.0 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage forms, each containing 1.0 milligrams of triazolam.

EXAMPLE 3

In this example, oxazepam was incorporated into a compressed dosage form. Oxazepam is a known potent lipophilic drug useful as an anxiolytic, an amnestic, and for sedating a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| citric acid | 1% | 0.2 |
| oxazepam | 1.5% | 0.3 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 25.17% | 5.03 |
| maltodextrin | 50.33% | 10.07 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage forms, each containing 30 milligrams of oxazepam.

EXAMPLE 4

In this example, lorazepam is incorporated into a compressed dosage form. Lorazepam is a known potent lipophilic drug useful as an anxiolytic, an amnestic, and for sedating a patient. Its high potency and lipophilicity makes it an excellent drug for transmucosal administration in accordance with the present invention.

A suitable mixture is prepared by combining the following ingredients as follows:

| Ingredient | % | grams |
|---|---|---|
| Lorazepam | 0.2% | 0.04 |
| citric acid | 1% | 0.2 |
| Ribotide | 2% | 0.4 |
| Compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 25.6% | 5.12 |
| maltodextrin | 51.2% | 10.24 |
| | 100% | 20 |

The ingredients are combined in a mixer in such a fashion as to ensure a uniform distribution of all ingredients within the mixture. Aliquots of 2 grams each are then hydraulically compressed around a commercially available wax-coated compressed paper holder, using a force sufficient to provide a final volume of 2 cubic centimeters. The procedure results in the preparation of 10 oral transmucosal dosage forms, each containing 4.0 milligrams of lorazepam.

EXAMPLE 5

In this example, etomidate was incorporated into a compressed dosage form. Etomidate is a known potent lipophilic drug useful as an anxiolytic, sedative and for anesthetizing a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| etomidate | 1% | 0.2 |
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 25.3% | 5.06 |
| maltodextrin | 50.7 | 10.14 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage forms, each containing 20 milligrams of etomidate.

EXAMPLE 6

In this example, thiamylal was incorporated into a compressed dosage form. Thiamylal is a known potent lipophilic drug useful as an anxiolytic, sedative and for anesthetizing a patient. Its high potency and lipophilicity makes it an excellent drug for transmucosal administration in accordance with the present invention.

A suitable mixture was prepared by combining the following ingredients as follows:

| Ingredient | % | grams |
| --- | --- | --- |
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| thiamylal sodium | 25% | 5.0 |
| maltodextrin | 32% | 6.4 |
| compressible sugar | 20% | 4.0 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage forms, each containing 0.5 grams of thiamylal.

EXAMPLE 7

The same procedure described with reference to Example 1 is used but levadopa is used in place of methohexital. Levadopa is used as necessary to treat Parkinson's Disease.

EXAMPLE 8

In this example, isosorbide dinitrate was incorporated into a compressed dosage form. In order to make 20 dosage forms of 2000 milligrams (2 grams), each containing 20 milligrams of isosorbide dinitrate (for a total formula weight of 20 grams), the following ingredients were combined:

| Ingredient | % | grams |
| --- | --- | --- |
| isosorbide dinitrate | 1% | 0.2 |
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 25.3% | 5.06 |
| maltodextrin | 50.7% | 10.14 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The foregoing procedure resulted in the preparation of 20 oral transmucosal dosage forms, each containing 10 milligrams of isosorbide dinitrate.

EXAMPLE 9

In this example, the same procedure as that described in Example 8 is followed except captopril is substituted for isosorbide dinitrate.

EXAMPLE 10

In this example, the same procedure as that described in Example 8 is followed except nifedipine was substituted for isosorbide dinitrate.

EXAMPLE 11

In this example, the same procedure as that described in Example 8 is followed except clonidine is substituted for isosorbide dinitrate.

EXAMPLE 12

In this example, the same procedure as that described in Example 8 is followed except esmolol is substituted for isosorbide dinitrate.

EXAMPLE 13

In this example, nitroglycerin was selected for incorporation into a compressed dosage form. Nitroglycerin is a potent lipophilic drug useful to control angina and blood pressure in perioperative hypertension, especially when associated with cardiovascular procedures and to produce controlled hypertension during surgical procedures.

The high potency and lipophilicity of the nitroglycerin make it an excellent drug for transmucosal administration in accordance with the present invention. A suitable mixture is prepared by combining 16 milligrams of nitroglycerin; 400 milligrams citric acid; 400 milligrams calcium stearate; 17.7 grams compressible sugar; 17.7 grams of maltodextrin; 600 milligrams peppermint microcaps; 1.2 grams cherry microcaps and 2 grams vanilla microcaps. Aliquots of 2000 milligrams each are then hydraulically compressed around a commercially available wax-coated compressed paper holder, using a force sufficient to provide a final volume of 2 cubic centimeters. The foregoing procedure results in the preparation of 20 lollipops, each containing 0.8 milligrams of nitroglycerin.

EXAMPLE 14

To make 10 dosage forms of 2000 milligrams (2 grams), each containing 10 mg of nifedipine (for a total formula weight of 20 grams) the following ingredients were combined:

| Ingredient | % | grams |
| --- | --- | --- |
| Ribotide | 1% | 0.2 |
| Compritol 888 | 5% | 1.0 |
| vanilla microcaps | 5% | 1.0 |
| vanilla cream microcaps | 5% | 1.0 |
| Nifedipine | 19.0% | 3.8 |
| Compressible sugar | 21.7% | 4.34 |
| Dextromaltrin | 43.3% | 8.66 |
| | 100% | 20 grams |

Appropriate changes in flavoring ingredients can be made in this formula to mask or optimize flavor perception in order to achieve ultimate acceptance of the dosage form by the desired patient group, be it adult, juvenile, pediatric, or neonate.

EXAMPLE 15

In this example, ergotamine is selected for incorporation into a compressed dosage form. Ergotamine is a potent lipophilic drug useful for relieving the pain associated with migraines. Its high potency and lipophilicity make it an excellent drug for transmucosal administration in accordance with the present invention.

A suitable matrix is prepared by combining 40 milligrams of ergotamine; 5.22 grams compressible sugar; 10.44 grams maltodextrin; 400 milligrams of Aspartame; 200 milligrams natural mint; 600 milligrams cherry; 1.0 gram artificial vanilla; 1.0 artifical vanilla cream; 300 milligrams ribotide; and 800 milligrams Compritol 888. Alloquats of 2000 milligrams each are then hydraulically compressed around a commercially available wax-coated compressed paper holder, using a force sufficient to provide a final volume of 2 cubic centimeters. The foregoing procedure results in the preparation of 10 lollipops, each containing 4 milligrams of ergotamine.

EXAMPLE 16

A drug-containing lollipop within the scope of the present invention to be used in the treatment of pain associated with oral candiasis is made according to the procedure of Example 15, except that the ingredients are combined in the following amounts.

| Ingredient | % | grams |
|---|---|---|
| Clotrimazole | 1.0% | 0.2 |
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificil vanilla cream | 5.0% | 1.0 |
| Compressed sugar | 25.83% | 5.17 |
| Maltodextrin | 51.67% | 10.33 |

The foregoing procedure results in the preparation of 10 lollipops, each containing 20 milligrams of clotrimazole.

EXAMPLE 17

A drug-containing lollipop within the scope of the present invention to be used in the treatment of pain associated with symptoms of esophagitis is made according to the procedure of Example 15, except that the ingredients are combined in the following amounts.

| Ingredient | % | grams |
|---|---|---|
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Compressed sugar | 9.5% | 1.9 |
| Maltodextrin | 19.0% | 3.8 |
| Al. sucrose sulfate | 50.0% | 10.0 |

The foreoing procedure results in the preparation of 10 lollipops, each containing 1 gram of aluminum sucrose sulfate.

EXAMPLE 18

A drug-containing lollipop within the scope of the present invention to be used in the treatment of pain associated with respiratory distress is made according to the procedure of Example 15, except that the ingredients are combined in the following amounts.

| Ingredient | % | grams |
|---|---|---|
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Oxtriphylline | 10.0% | 2.0 |
| Compressed sugar | 22.83% | 4.57 |
| Maltodextrin | 45.67% | 9.13 |

The foregoing procedure results in the preparation of 10 lollipops, each containing 200 milligrams of oxtriphylline.

EXAMPLE 19

A drug-containing lollipop within the scope of the present invention to be used in the treatment associated with patients experiencing nausea and vomiting is made according to the procedure of Example 15, except that the ingredients are combined in the following amounts.

| Ingredient | % | grams |
|---|---|---|
| Natural mint | 1.0% | 0.2 |
| Ribotide | 1.5% | 0.3 |
| Aspartame | 2.0% | 0.4 |
| Meclizine | 2.5% | 0.5 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Compressed sugar | 25.33% | 5.07 |
| Maltodextrin | 50.67% | 10.13 |

The foregoing procedure results in the preparation of 10 lollipops, each containing 50 milligrams of meclizine.

EXAMPLE 20

A drug-containing lollipop within the scope of the present invention to be used in the treatment of the symptoms associated with polyuria is made according to the procedure of Example 15, except that the ingredients are combined in the following amounts.

| Ingredient | % | grams |
|---|---|---|
| Desmopressin | 0.001 | 0.0002 |
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Compressed sugar | 26.17% | 5.234 |
| Maltodextrin | 52.33% | 10.47 |

The foregoing procedure results in the preparation of 10 lollipops, each containing 20 micrograms of desmopressin.

EXAMPLE 21

A drug-containing lollipop within the scope of the present invention to be used in the treatment of the symptoms of Parkinson's Disease is made according to the procedure of Example 15, except that the ingredients are combined in the following amounts.

| Ingredient | % | grams |
| --- | --- | --- |
| Natural mint | 1.0% | 0.2 |
| Carbidopa | 1.25% | 0.25 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Levodopa | 12.5% | 2.5 |
| Compressed sugar | 21.58% | 4.32 |
| Maltodextrin | 43.17% | 8.63 |

The foregoing procedure results in the preparation of 10 lollipops, each containing 25 milligrams of carbidopa and 250 milligrams of levodopa.

EXAMPLE 22

A drug-containing lollipop within the scope of the present invention to be used to induce labor or reduce postpartum hemorrhage is made according to the procedure of Example 15, except that the ingredients are combined in the following amounts.

| Ingredient | % | grams |
| --- | --- | --- |
| Oxytocin | 0.001% | 0.0002 |
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Compressed sugar | 26.17% | 5.234 |
| Maltodextrin | 52.33% | 10.466 |

The foregoing procedure results in the preparation of 10 lollipops, each containing 20 micrograms of oxytocin.

EXAMPLE 23

A drug-containing lollipop within the scope of the present invention to be used in the treatment of the symptoms of diabetes is made according to the procedure of Example 15, except that the ingredients are combined in the following amounts.

| Ingredient | % | grams |
| --- | --- | --- |
| Insulin | 0.05% | 0.01 |
| Natural mint | 1.0% | 0.2 |
| Ribotide | 1.5% | 0.3 |
| Aspartame | 2.0% | 0.4 |
| Wild cherry | 3.0% | 0.6 |
| Compritol 888 | 4.0% | 0.8 |
| Artificial vanilla | 5.0% | 1.0 |
| Artificial vanilla cream | 5.0% | 1.0 |
| Compressed sugar | 26.15% | 5.23 |
| Maltodextrin | 52.3% | 10.46 |

The foregoing procedure results in the preparation of 10 lollipops, each containing the equivalent of 30 units of insulin.

6. Summary

In summary, it can be seen that the present invention accomplishes the objects set forth above. The present invention provides compositions and methods of manufacture for administering a drug in a precise dose in order to obtain a rapid effect. In addition, the present invention provides methods for forming a drug containing candy matrix having the following attributes:

(1) drugs having relatively low melting points can be used without degrading the drug;
(2) disagreeable flavor characteristics can be masked;
(3) insoluble ingredients can be used;
(4) chemically incompatible ingredients can be used;
(5) buffers can be added to optimize the ratio of ionized and nonionized drug form;
(6) chemical agents to modify the dissolution characteristics of the drug can be added;
(7) dissolution characteristics can be modified mechanically by changing the compressive forces used to form the lollipop;
(8) stratification of active ingredients can be accomplished; and
(9) the dosage can be modified by utilizing an assembly of dosage units onto a holder.

The present invention, therefore, provides the ability to provide precise control over the dosage and effect of the drug. This is obtained by transmucosal administration by sucking on a lollipop containing the drug. As a result, the precise dosage and effect can be obtained.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for producing a drug-containing lollipop for use in transmucosal delivery of the drug to a patient, the method comprising the steps of:
   (a) obtaining a pharmacologically effective dose of the drug in a substantially powdered form, the drug being capable of absorption through mucosal tissues of the mouth, pharynx, and esophagus;
   (b) obtaining a soluble carbohydrate material capable of forming a compressible confectionary matrix and capable of dissolving in the mouth of the patient;
   (c) mixing the drug and the carbohydrate material at a temperature below the melting points of the drug and the carbohydrate material to form a drug-containing matrix such that the drug is dispersed substantially throughout the matrix, the drug-containing matrix being capable of releasing the drug for absorption through the mucosal tissues upon dissolution of the matrix in the mouth of the patient;
   (d) compressing the drug-containing matrix in a mold to form an integral mass such that, when the integral mass dissolves in the mouth of the patient, the drug is released for absorption through the mucosal tissues; and
   (e) incorporating a holder as part of the integral mass in order to form the drug-containing lollipop.

2. A method for producing a drug-containing lollipop for use in transmucosal delivery of the drug to a patient as defined in claim 1 wherein a buffer is added to the drug-containing matrix.

3. A method for producing a drug-containing lollipop for use in transmucosal delivery of the drug to a patient as defined in claim 2 wherein the buffer modifies the pKa of the drug such that, when the integral mass is dissolved, a majority of the drug remains non-ionized in order to facilitate transmucosal absorption of the drug.

4. A method for producing a drug-containing lollipop for use in transmucosal delivery of the drug to a patient as defined in claim 3 wherein the buffer is citric acid/sodium citrate.

5. A method for producing a drug-containing lollipop for use in transmucosal delivery of the drug to a patient as defined in claim 1 wherein the drug has sufficient lipophilic properties such that the drug can be absorbed through the mucosal tissue.

6. A drug-containing lollipop for use in transmucosal delivery of the drug to a patient comprising:
- a soluble, compressible carbohydrate material;
- a pharmacologically effective dose of a drug in a substantially powdered form, the drug being capable of absorption through mucosal tissues of the mouth, pharnyx, and esophagus and being dispersed substantially uniformly throughout the carbohydrate material at a temperature below the melting points of the drug and the carbohydrate material and compressed with the carbohydrate material into a solid integral mass which is capable of dissolving in the mouth of the patient so that the drug is released for absorption through mucosal tissues of the mouth, pharnyx, and esophagus upon dissolution of the integral mass in the mouth of the patient;
- holder means secured to the integral mass so as to form a drug-containing lollipop, the holder means being configured so as to permit convenient insertion and removal of the drug-containing integral mass into and out of the mouth of a patient.

7. A method for producing a drug-containing lollipop for use in transmucosal delivery of the drug to a patient as defined in claim 1 wherein the holder is incorporated into the integral mass by compression of the drug-containing matrix around the holder during compressing step (d).

8. A method for producing a drug-containing lollipop for use in transmucosal delivery of the drug to a patient as defined in claim 1 wherein the holder is incorporated as part of the integral mass by affixing the holder to the integral mass after compressing step (d).

9. A method for producing a drug-containing lollipop for use in transmucosal delivery of the drug to a patient as defined in claim 1 wherein the soluble carbohydrate material in the drug-containing matrix includes compressible confectionary sugar.

10. A method for producing a drug-containing lollipop for use in transmucosal delivery of the drug to a patient as defined in claim 9 wherein the drug-containing matrix includes a lubricating agent such that the integral mass can be released from the mold after compressing step (d).

11. A method for producing a drug-containing lollipop for use in transmucosal delivery of the drug to a patient as defined in claim 1 wherein the drug-containing matrix includes at least one flavor enhancer.

12. A method for producing a drug-containing lollipop for use in transmucosal delivery of the drug to a patient as defined in claim 1 wherein the drug-containing matrix includes maltodextrin in order to aid in dissipating any unpleasant flavors of the drug.

13. A method for producing a drug-containing lollipop for use in transmucosal delivery of the drug to a patient as defined in claim 1 wherein a substantially water-insoluble component is added to the drug-containing matrix such that the dissolution of the integral mass in the mouth of the patient is made slower by the substantially water-insoluble component in the drug-containing matrix.

14. A method for producing a drug-containing lollipop for use in transmucosal delivery of the drug to a patient as defined in claim 1 wherein the confectionary mixture is compressed with forces in the range of from about 2000 newtons to about 5000 newtons.

15. A method for producing a drug-containing lollipop for use in transmucosal delivery of the drug to a patient as defined in claim 1 wherein the drug is methohexital.

16. A method for producing a drug-containing lollipop for use in transmucosal delivery of the drug to a patient as defined in claim 1 wherein the drug is selected from the group consisting of triazolan, oxazepam, lorazepam, etomidate, and thiamylal.

17. A method for producing a drug-containing lollipop for use in transmucosal delivery of the drug to a patient as defined in claim 1 wherein the drug is nitroglycerin.

18. A method for producing a drug-containing lollipop for use in transmucosal delivery of the drug to a patient in a dose-to-effect manner, the method comprising the steps of:
- (a) obtaining a pharmacologically effective dose of the drug in a substantially powdered lipophilic form capable of absorption through mucosal tissues of the mouth, pharnyx, and esophagus;
- (b) obtaining a soluble carbohydrate material capable of forming a compressible confectionary matrix and capable of dissolving in the mouth of the patient;
- (c) obtaining a buffer capable of modifying the pKa of the drug such that a majority of the drug remains non-ionized in order to facilitate transmucosal absorption of the drug;
- (d) mixing the drug, the soluble carbohydrate material, and the buffer at a temperature below the melting points of the drug and the carbohydrate material to form a solid drug-containing matrix such that the drug is dispersed substantially throughout the matrix, the drug-containing matrix being capable of releasing the drug for absorption through the mucosal tissues upon dissolution of the matrix in the mouth of the patient;
- (e) compressing the drug-containing matrix in a mold to form an integral mass such that when the integral mass dissolves in the mouth of the patient, the drug is released for absorption through the mucosal tissues such that the drug is administered in a dose-to-effect manner; and
- (f) incorporating a holder as part of the integral mass in order to form the drug-containing lollipop.

19. A method for producing a drug-containing lollipop for use in transmucosal delivery of the drug to a patient as defined in claim 18 wherein the holder is incorporated into the integral mass by compression of the drug-containing matrix around the holder during compressing step (e).

20. A method for producing a drug-containing lollipop for use in transmucosal delivery of the drug to a patient as defined in claim 18 wherein the holder is incorporated as part of the integral mass by affixing the holder to the integral mass after compressing step (e).

21. A method for producing a drug-containing matrix for use in transmucosal delivery of the drug to a patient as defined in claim 18 wherein the drug-containing mixture includes maltodextrin in order to aid in dissipating any unpleasant flavors of the drug.

22. A method for producing a drug-containing matrix for use in transmucosal delivery of the drug to a patient as defined in claim 18 wherein the buffer comprises citric acid/sodium citrate.

23. A method for producing a drug-containing matrix for use in transmucosal delivery of the drug to a patient as defined in claim 18 wherein the drug-containing matrix includes compressible sugar.

24. A method for producing a drug-containing matrix for use in transmucosal delivery of the drug to a patient as defined in claim 18 wherein the drug-containing matrix includes a flavoring ingredient.

25. A method for producing a drug-containing matrix for use in transmucosal delivery of the drug to a patient as defined in claim 18 wherein the confectionary mixture is compressed with forces in the range of from about 2000 newtons to about 5000 newtons.

26. A method for producing a drug-containing matrix for use in transmucosal delivery of the drug to a patient as defined in claim 18 wherein the drug is methohexital.

27. A method for producing a drug-containing matrix for use in transmucosal delivery of the drug to a patient as defined in claim 18 wherein the drug is selected from the group consisting of triazolan, oxazepam, lorazepam, etomidate and thiamylal.

28. A method for producing a drug-containing matrix for use in transmucosal delivery of the drug to a patient as defined in claim 18 wherein the drug is selected from the group consisting of isosorbide dinitrate, captopril, nifedipine, clonidine, and esimolol.

29. A method for producing a drug-containing matrix for use in transmucosal delivery of the drug to a patient as defined in claim 18 wherein the drug is nitroglycerin.

30. A method for producing a drug-containing matrix for use in transmucosal delivery of the drug to a patient as defined in claim 18 wherein the drug is a potent, fast-acting drug.

31. A method for producing a drug-containing matrix for use in transmucosal delivery of the drug to a patient as defined in claim 30 wherein the drug has effects on the central nervous system of the patient.

32. A method for producing a drug-containing matrix for use in transmucosal delivery of the drug to a patient as defined in claim 30 wherein the drug has effects on the cardiovascular system of the patient.

33. A method for producing a drug-containing matrix for use in transmucosal delivery of the drug to a patient as defined in claim 30 wherein the drug has effects in the renal vascular system of the patient.

34. A method for producing a drug-containing matrix for use in transmucosal delivery of the drug to a patient as defined in claim 20 wherein the materials in the drug-containing matrix includes a lubricating agent such that the integral mass can be released from the mold after compressing step (d).

35. A method for producing a drug-containing matrix for use in transmucosal delivery of the drug to a patient as defined in claim 34 wherein the lubricating agent comprises glyceryl behenate.

36. A method for producing a drug-containing matrix for use in transmucosal delivery of the drug to a patient as defined in claim 34 wherein the releasing agent is a substantially water-insoluble component such that the dissolution of the integral mass in the mouth of the patient is made slower by the substantially water-insoluble component in the drug-containing matrix.

37. A drug-containing lollipop for use in transmucosal delivery of the drug to a patient, said composition comprising:

a soluble, compressible, substantially powdered carbohydrate material;

a pharmacologically effective dose of a lipophilic drug in a substantially powdered form, the drug being capable of absorption through mucosal tissues of the mouth, pharnyx, and esophagus and being dispersed substantially uniformly throughout the carbohydrate material at a temperature below the melting points of the drug and the carbohydrate material and compressed with the carbohydrate material into a solid integral mass which is capable of dissolving in the mouth of the patient so that the drug is released for absorption through mucosal tissues of the mouth, pharnyx, and esophagus upon dissolution of the integral mass in the mouth of the patient;

a buffer which is also dispersed substantially uniformly throughout the integral mass, the buffer being capable of modifying the pKa of the drug such that a majority of the drug remains non-ionized in order to facilitate transmucosal absorption of the drug; and holder means secured to the integral mass so as to form a drug-containing lollipop, the holder means being configured so as to permit convenient insertion and removal of the drug-containing integral mass into and out of the mouth of a patient.

38. A drug-containing lollipop for use in transmucosal delivery of the drug to a patient as defined in claim 37, wherein the buffer is citric acid/sodium citrate.

39. A drug-containing lollipop for use in transmucosal delivery of the drug to a patient as defined in claim 37, wherein the soluble carbohydrate material in the drug-containing integral mass includes compressible confectionary sugar.

40. A drug-containing lollipop for use in transmucosal delivery of the drug to a patient as defined in claim 39, wherein the drug-containing integral mass further includes a lubricating agent dispersed substantially uniformly throughout the integral mass in order to aid in the manufacture of the drug-containing lollipop.

41. A drug-containing lollipop for use in transmucosal delivery of the drug to a patient as defined in claim 39, wherein the drug-containing integral mass further includes maltodextrin dispersed substantially uniformly throughout the integral mass in order to aid in dissipating any unpleasant flavors of the drug in the integral mass.

42. A drug-containing lollipop for use in transmucosal delivery of the drug to a patient as defined in claim 41, wherein the drug-containing integral mass further comprises at least one flavor enhancer dispersed substantially uniformly throughout the integral mass.

43. A drug-containing lollipop for use in transmucosal delivery of the drug to a patient as defined in claim 37, wherein the drug-containing integral mass further comprises a substantially water-insoluble component dispersed substantially uniformly throughout the integral mass in order to slow the dissolution of the integral mass in the mouth of the patient.

44. A method for producing a drug-containing lollipop for use in transmucosal delivery of the drug to a patient as defined in claim 18 further comprising the step of mixing at least one flavoring with the drug-containing matrix.

45. A method for producing a drug-containing lollipop for use in transmucosal delivery of the drug to a patient as defined in claim 18 further comprising the step of mixing at least one flavor enhancer with the drug-containing matrix.

46. A method for producing a drug-containing lollipop for use in transmucosal delivery of the drug to a patient as defined in claim 15 wherein the drug-containing matrix comprises from about 10 milligrams to about 500 milligrams of methohexital.

47. A method for producing a drug-containing lollipop for use in transmucosal delivery of the drug to a patient as defined in claim 26 wherein the drug-containing matrix comprises from about 10 milligrams to about 500 milligrams of methohexital.

48. A drug-containing lollipop for use in transmucosal delivery of the drug to a patient as defined in claim 37 further comprising at least one flavoring.

49. A drug-containing lollipop as defined in claim 6 further comprising at least one flavoring dispersed within said integral mass.

50. A drug-containing lollipop as defined in claim 3 further comprising at least one releasing agent dispersed within said integral mass.

51. A drug-containing lollipop as defined in claim 6 further comprising at least one flavor enhancer dispersed within said integral mass.

52. A drug-containing lollipop as defined in claim 6 further comprising at least one sweetener in addition to said carbohydrate material dispersed within said integral mass.

* * * * *